United States Patent [19]

Sundberg et al.

[11] Patent Number: 5,204,352

[45] Date of Patent: Apr. 20, 1993

[54] COMPOUNDS EXHIBITING ANTI-PARASITIC ACTIVITY AND A METHOD FOR THEIR USE

[75] Inventors: Richard J. Sundberg, Charlottesville, Va.; Daniel J. Dahlhausen, Columbus, Ohio; Govindarajan Manikumar, Raleigh, N.C.; Babu J. Mavunkel, Baltimore; Hikmat A. Musallam, Damascus, both of Md.; Atanu Biswas, Cleveland; Srinivasan Varadarajan, Stow, both of Ohio

[73] Assignee: The United States of America as represented by the Secretary of the Army, Washington, D.C.

[21] Appl. No.: 102,445

[22] Filed: Sep. 29, 1987

[51] Int. Cl.$^5$ ................... A61K 31/435; C07D 471/04
[52] U.S. Cl. ................... 514/258; 514/292; 514/300; 514/301; 514/396; 514/400; 544/281; 546/84; 546/121; 548/154; 548/335; 548/343.1; 548/343.5; 548/342.5; 548/346.1; 548/306.4; 548/310.7; 548/304.4; 548/330.1; 548/327.1; 548/341.1
[58] Field of Search ................... 546/121, 84; 544/281; 548/154, 335, 338, 339, 342, 346; 514/258, 292, 300, 301, 396, 400

[56] References Cited

U.S. PATENT DOCUMENTS 4,044,015  8/1977  Kuhle ................... 546/121

OTHER PUBLICATIONS

Winkelmann et al.–Forsch/Drug Research, 28(I) No. 5 (1978), pp. 739–749, Ellrich et al., J. Med. Chem., 27, pp. 35–40 (1984).

Primary Examiner—Bernard Dentz
Attorney, Agent, or Firm—Werten F. W. Bellamy; John Francis Moran

[57] ABSTRACT

Novel compounds are provided which exhibit high levels of anti-parasitic activity, specifically against parasites of the genus Trypanosoma. The compounds are comprised of aryl-substituted quaternary heteroaromatic salts which include a positively charged imidazolium or other heterocyclic ring, a linking group, a phenyl ring, and a polar functional group. The polar functional group is preferably a quanylhydrazone or a heterocyclic hydrazone. A method is also provided for treating the diseases associated with Trypanosoma parasites which comprises administering to infected animals or humans an effective amount of a compound of the present invention.

20 Claims, No Drawings

COMPOUNDS EXHIBITING ANTI-PARASITIC ACTIVITY AND A METHOD FOR THEIR USE

FIELD OF THE INVENTION

The invention relates to compounds and a method for combatting parasitic infections in animals and man. In particular, the invention relates to novel aryl-substituted quaternary heteroaromatic salts which exhibit anti-parasitic activity against *Trypanosoma rhodesiense*, the parasite responsible for causing veterinary and human trypanosomiasis.

BACKGROUND OF THE INVENTION

One of the more troublesome parasites known in the world today are the trypanosomes. The trypanosomes comprise a group of flagellate protozoans of the genus Trypanosoma that often live as parasites in the blood of man and other vertebrates. These deadly pathogens are usually transmitted through insect bites, and can cause a wide range of serious diseases in humans and animals. Although at present there are several compounds known for fighting trypanosomiasis, such as berenil and pentamidine, the current range of drugs against this disease suffer from drawbacks such as toxicity, various undesirable side effects, need for high dosage levels, and even development of a resistance to certain drugs by the parasites. What is desired is a compound which exhibits high levels of anti-parasitic activity, yet at the same time is safe, convenient, non-toxic, and minimizes the occurrence of harmful side effects.

SUMMARY OF THE INVENTION

A series of novel compounds that exhibit high levels of anti-parasitic activity against parasites of the genus Trypanosoma are provided which comprise aryl-substituted quaternary heteroaromatic salts. These salts are comprised of a positively charged imidazolium or other heterocyclic ring, a linking group, a phenyl ring, and a polar functional group, optimally a guanylhydrazone or a heterocyclic hydrazone. A method is also provided for fighting the pathological effects of the trypanosome parasites which comprises administering to infected humans or animals an effective amount of a quaternary heteroaromatic salt of the present invention.

DETAILED DESCRIPTION OF THE PREFERRED EMBODIMENTS

The aryl-substituted quaternary heteroaromatic salts of the present invention which exhibit high levels of anti-parasitic activity are compounds having one of the following two general formulas:

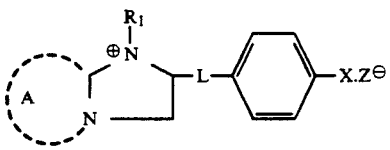

wherein A represents an optional heterocyclic ring extending from the imidazolium ring, $R_1$ is a straight or branched aliphatic group having from one to ten carbon atoms, L is a linking group, and X is a polar functional group; or

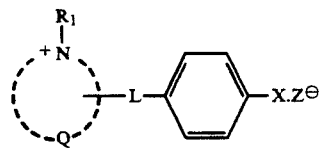

wherein $R_1$, L and X are as defined in formula I above, and wherein Q represents a heterocyclic ring which includes the quaternary nitrogen. These groups of compounds typically are produced with a negatively charged counterion which forms physiologically acceptable salts with the compounds.

In compound I above, the heterocyclic ring A is preferably a pyridine ring. Ring A can also be a thiazole ring or a pyrimidine ring, or it can be absent from the compound, leaving the imidazolium ring to stand alone. $R_1$, which is linked to a nitrogen on the imidazolium ring, is preferably a methyl group, but many other aliphatic groups, such as propenyl, ethyl, isopropyl, etc., are suitable here. The linking group L can be any suitable carbon intervening group, such as $—OCH_2—$ or $—CH=CH—$, or it may just comprise a single bond between the imidazolium ring and the phenyl group.

The polar functional group X of the compounds of formulas I and II is optimally a quanylhydrazone, a substituted guanylhydrazone, or a heterocyclic hydrazone. Other polar functionalities useful in the present invention include amido, thiocarboxamide, carboxamidine, amide oxime, and other compounds derived from the carboxaldehyde functional group, such as semicarbazones and thiosemicarbazones.

In compound II above, the quaternary heterocyclic ring Q is preferably a pyridinium ring. However, a number of suitable heterocyclic rings, such as thiazolium or benzimidazolium, can be substituted for the pyridinium ring.

To prepare the compounds of the present invention, several steps based on modifications in presently used methodology are necessary. In general, the chemical preparations involve: (1) construction of the neutral heteroaromatic compound with a functional group appropriate for eventually introducing the required polar substituent group; (2) chemical modification of the functional group; (3) introduction of the quaternary substituent on a nitrogen atom of the heteroaromatic ring; and (4) final introduction of the polar substituent by reaction at the modified functional group. The sequence of transformation can be modified as required by individual examples.

The compounds are preferably prepared using one of the following routes:

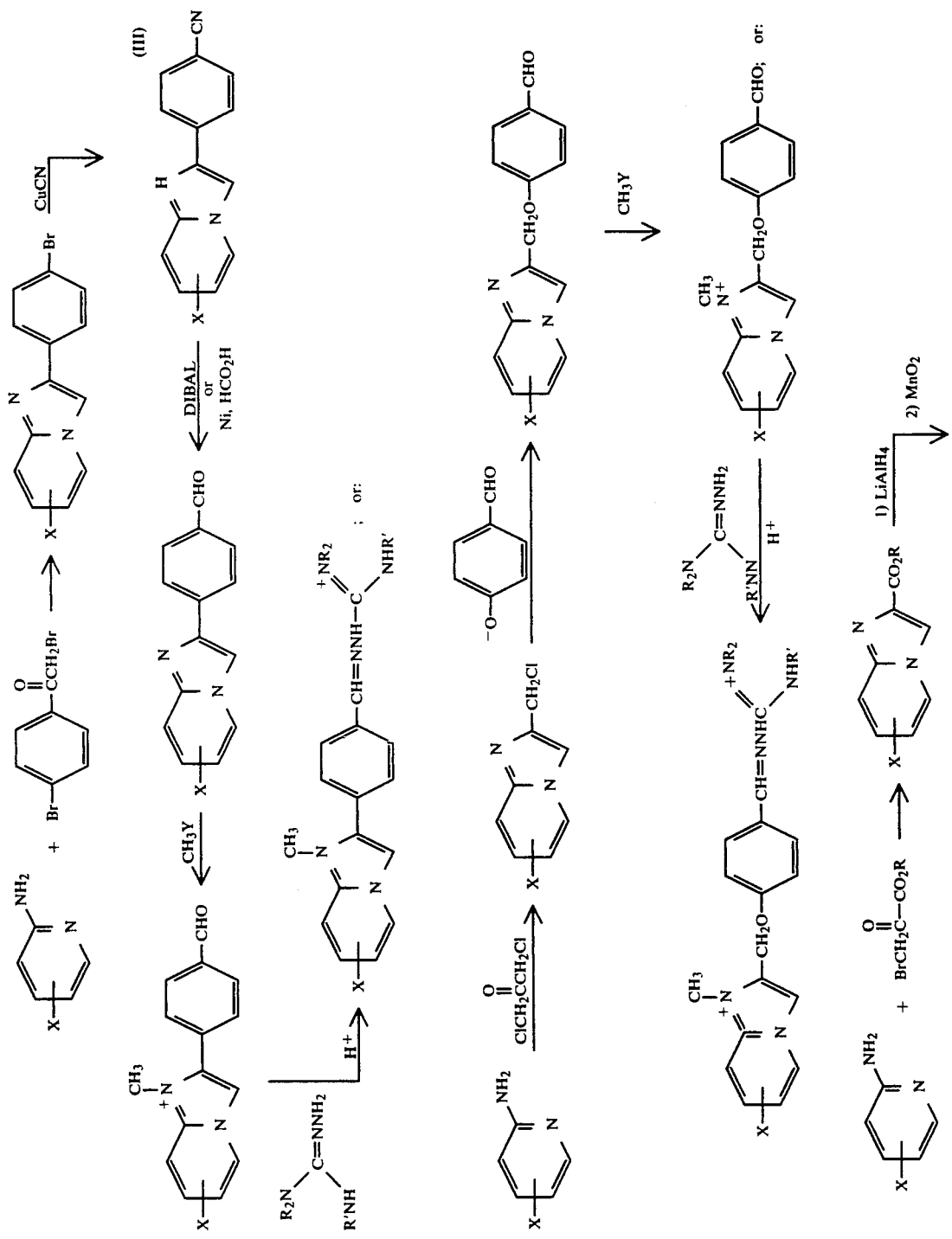

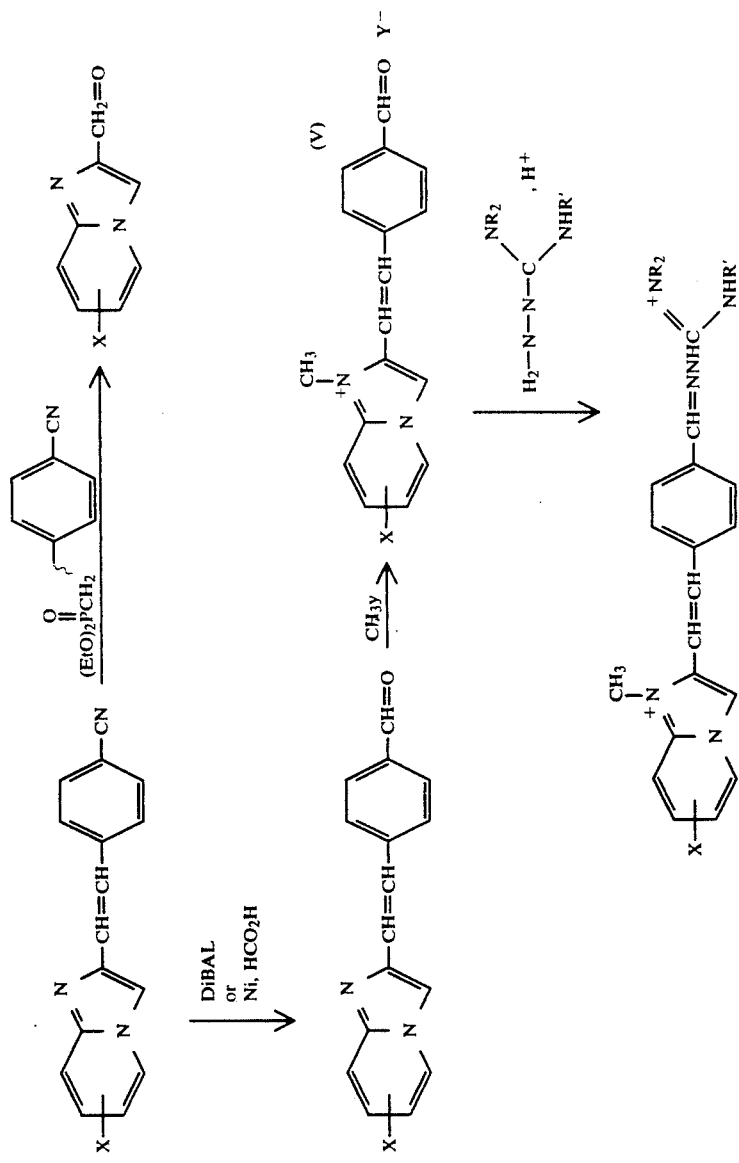

In general, the final step in the above process is carried out by mixing together the desired compounds and stirring or refluxing at a temperature of 25°–120° C. for up to 24 hours in a suitable organic solvent. A precipitated product will form as the solution is cooled, or in some cases, the desired compounds are obtained after evaporation of the solvent. The collected precipitate is then preferably recrystallized from ethanol or other suitable solvent.

The products formed are typically dications and are isolated as salts with bromide, arenesulfonate or other counterions. In some instances the functional group X is non-basic, in which case monocations are isolated. In other cases, the functional group Z contains a second basic functionality, in which case dications are obtained. The materials are solids with good to fair water solubility.

As an example of the preparation of a compound of the present invention, a 1,3-dimethyl-2-(4'-formylphenyl)imidazole guanylhydrazone tosylate was prepared starting with 500 mg of 1,3-dimethyl-2-(4'-formylphenyl)imidazolium tosylate. To this starting material was added 275 mg of aminoguanidine bicarbonate and 380 mg of p-toluenesulfonic acid in 30 ml abs. ethanol. The mixture was stirred for 24 hours and then refluxed for 6 hours. The product was filtered and recrystallized from ethanol containing a little water. The yield was 0.50 g of a solid product having a melting point of 214°–215° C. Other examples of the preparation of compounds of the present invention are provided at the end of the specification.

The compounds of the present invention have been evaluated for their effect on parasitic activity, and many of the compounds show significant life-extending and curative activity when administered to infected animals. According to the present invention a method of treating parasitic diseases in man and animals is provided which comprises administering an effective amount of a compound of formula I above to humans or animals. By effective amount of this compound is meant that amount which is needed to cause some reduction in parasitic activity in an infected animal. It has been observed that curative activity occurs for some compounds of the present invention when administered in dosages of as little as about 0.2 mg/kg of the animal. For example, the 2-(3,4,5,6-tetrahydropyrimidyl)hydrazone of 1,6-dimethyl-2-(4'-formylphenyl)imidazo[1,2-a]-pyridinium bromide is curative at 0.21 mg/kg, and is tolerated up to a dose of about 100 mg/kg.

The preferred mode of administration of these compounds is subcutaneously. With subcutaneous administration, however, many of the compounds show lethal toxicity at very high dosage amounts. Thus, it is also possible to administer these compounds peritoneally. Compounds which are subcutaneously active are generally peritoneally active at higher doses. Further, none of the compounds administered peritoneally have shown lethal toxicity at dosages up to 400 mg/kg.

The compounds of the present invention were evaluated biologically in vivo with groups of 5 mice at various dose levels. The results of these evaluations are shown in Table 1. Unless otherwise indicated, the data are for subcutaneous administration. Dose levels marked with an asterisk are for peritoneal administration in a HEC+T medium. In addition, Table 2 present results of peritoneal administration with substituted quanylhydrazones. The biological evaluation was done according to a standard protocol based on the method described by Rane et al., *Amer. J. Trop. Med Hyg.* 25:395 (1976). The results indicate that many of the compounds of the present invention exhibit significant levels of life-extending and curative activity.

The mechanism of action and nature of toxicity of the compounds is not known. It has been observed that the active compounds typically inhibit both thymidine and leucine uptake in in vitro assays of *T. rhodesiense*. The compounds are structurally distinct from all previously known trypanocides but may be related to previously known bis-amidine and bis-guaylhydrazones which show trypanocidal activity. Compounds in this class include berenil, pentamidine, DAPI (2-phenylindole-5-4'-bis-carboxamidine), aminocarbilide, and m-diacetylbenzene-bis-guanylhydrazone.

The range of anti-parasitic activity beyond African trypanosomiasis is not known. The compounds are 10–50 times more active on a dose/body weight basis in the *T. rhodesiense* in vivo mouse screen than berenil or pentamidine. Depending upon toxicity, it would appear that the compounds would be competitive with berenil and pentamidine for treatment of veterinary and/or human trypanosomiasis.

The activity data, as presented in Tables 1 and 2 show that significant variation in the compounds of the present invention can be made, and yet the anti-parasitic biological activity is retained. These variations include, but are not limited to: (1) introduction of substituents at the various positions on the quaternary heteromatic ring; (2) variation of the polar substituent attached to the aromatic ring; and (3) changes in the heteroaromatic ring itself. Molecular features which are required for activity appear to be an aryl-substituted, quaternary heteroaromatic system in which the aryl-substituent is further substituted by a polar functional group. Once produced, the quaternary heteroaromatic compounds of the present invention are effective in fighting parasitic activity of parasites of the genus Trypanosoma, and likely will be useful in fighting diseases caused by other similar organisms, such as those in the class Kinetoplasida.

The following examples are presented as illustrative of the present invention only, and should not be construed as limiting the invention in any way.

EXAMPLE 1

Preparation of 6-Methyl-2-(4'-bromophenyl)imidazo-[1,2-a]pyridine

A mixture of 18.8 g of 2-amino-5-methylpyridine and 27.8 g of p-bromophenacyl-bromide in 200 ml of acetone was refluxed for 8 hrs. The precipitate was collected and dissolved in hot methanol and 2 ml of concentrated HBr was added. The methanol solution was then basified with ammonium hydroxide. The precipitated product was collected and recrystallized from ethanol; yield 18.5 g (68%); mp 215°–216° C.

EXAMPLE 2

Preparation of 6-Methyl-2-(4'-cyanophenyl)imidazo-[1,2-a]pyridine

6-Methyl-2-(4'-bromophenyl)imidazo[1,2-a]pyridine (6.0 g) was mixed with 3.0 g of CuCN and 50 ml DMF. The mixture was refluxed for 24 hrs. The hot solution was then poured into a (1:4) ethylenediamine-water mixture (200 ml). Using chloroform, the compound was extracted. The chloroform layer was washed with water, dried and evaporated. The residue was crystallized and recrystallized from ethanol; yield; 3.4 g (69%); mp 225°-226° C.

EXAMPLE 3

Preparation of 6-Methyl-2-(4'-formylphenyl)imidazo-[1,2-a]pyridine 1.0 g of 6-methyl-2-(4'-cyanophenyl)imidazo[1,2-a]pyridine in 20 ml dry benzene was treated with Dibal (5.5 ml of 1M solution). After stirring for 2-3 hrs, methanol 15 ml was added, followed by 10 ml of 10% $H_2SO_4$. The precipitate was filtered, dissolved in water and basified with 15% NaOH. The collected precipitate was recrystallized from ethanol. Yield 0.68 g (68%); mp 210°-211° C.

EXAMPLE 4

Preparation of 1,6-Dimethyl-2-(4'-formylphenyl)imidazo-[1,2-a]-pyridinium tosylate A mixture of 4.0 g of the aldehyde and 4.0 gm of methyl tosylate in 30 ml acetonitrile was refluxed for 24 h. Cooling and filtration gave fine needle shape crystals of the tosylate in 76% yield. In subsequent preparations the tosylate was obtained as an oil which was used after thorough extraction with ether to remove methyl tosylate.

EXAMPLE 5

Preparation of 1,6-Dimethyl-2-(4'-formylphenyl)imidazo-[1,2-a]pyridine guanylhydrazone ditosylate 1,6-Dimethyl-2-(4'-formylphenyl)imidazo[1,2-a]-pyridinium tosylate (1 g), 350 mg of aminoguanidine and 400 mg of p-toluenesulfonic acid were dissolved in ethanol (10 ml) and mildly refluxed for 2-3 hours. The solution was then stirred at room temperature overnight. The precipitated material was filtered and recrystallized from ethanol-acetone-ether. Yield 1 g (69%); mp 232°-233° C.

Anal. Calcd. for $C_{31}H_{34}N_6S_2O_6.H_2O$:
Calcd.: C, 55,57; H, 5,43; N, 12,57; Found C, 55.61: H, 5.44; N, 12.56.

EXAMPLE 6

Preparation of 2-(4'-Cyanophenyl)imidazo[2,1-]-thiazole

A mixture of 20.0 g of 2-(4'-iodophenyl)imidazo-[2,1-b]thiazole and CuCN (10 g) in 150 ml pyridine was refluxed for 24 hours. The hot mixture was poured into 500 ml of a solution of ethylenediamine in water (1:4). The mixture was stirred well, and filtered. The solid was collected and stirred in 10% NaCN solution. The solid was again collected by filtration and washed with water. The product was recrystallized from ethanol to yield 11 g (79%) of product, mp 201° C.

EXAMPLE 7

Preparation of 2-(4'-Formylphenyl)imidazo[2,1-b]-thiazole 2-(4'-Cyanophenyl)imidazo[2,1b]thiazole (6 g) was dissolved in 100 ml of benzene (dry). 33 ml of 1M diisobutylaluminumhydride was added carefully under $N_2$. The reaction mixture was stirred for 3 hours. About 50 ml methanol was then added, followed by 70 ml of 10% $H_2SO_4$. The precipitate which formed was collected. It was dissolved in $H_2O$ and basified with 50% NaOH solution. The free aldehyde which precipitated was collected and recrystallized from ethanol. Yield 4.5 gm (75%), mp 169° C.

EXAMPLE 8

Preparation of 1-Methyl-2-(4'-formylphenyl)imidazo-[2,1-b]thiazolium tosylate

A mixture of 1.0 g of 2-(4'-formylphenyl)imidazo-[2,1-b]thiazole and 1.0 g of methyl tosylate in 10 ml of dry $CH_3CN$ was refluxed for 20 hours. The solution was then evaporated to dryness. The residue was dissolved in hot water and extracted with chloroform to remove excess methyl tosylate. The aqueous layer was evaporated and the residue was recrystallized from acetone. Yield 1.4 gm (77%); mp 195° C.

EXAMPLE 9

Preparation of 1-Methyl-2-(4'-formylphenyl)imidazo-[2,1-b]thiazole guanylhydrazone ditosylate A mixture of 1.0 g of the aldehyde monotosylate, 0.37 g aminoguanidine (10% excess) and 0.53 g of p-toluenesulfonic acid monohydrate (10% excess) in 15 ml EtOH was gently refluxed for one hour. On cooling to room temperature the guanylhydrazone precipitated. The product was recrystallized from acetonitrile. Yield 1.1 g (71%); 229°-231° C.

EXAMPLE 10

Preparation of 1-Methyl-2-(4'-formylphenyl)imidazo-[2,1-b]thiazolium 3-(1,2,4-triazolyl)hydrazone dibromide 2-(4'-formylphenyl)imidazo[2,1-b]thiazolium tosylate (2 g) was mixed with 0.82 g of 3-hydrazino-1,2,4-thiazole HBr in 25 ml of ethanol and refluxed for 2 hours. 1 ml of conc HBr was then added and the mixture was stirred for 12 hours. The precipitate was filtered and recrystallized by dissolving in hot ethanol containing a few drops of water. After concentrating and cooling this solution the product crystallized. Yield 1.82 g (72%); mp 282° C.

Anal. Calcd. for $C_{15}H_{15}N_7SBr_2.2H_2O$:
Calcd: C, 34.56; H, 3.67; N, 18,81; Found: C, 34.78; H, 3.67; N, 18.90.

TABLE I

| | | | Trypanocidal Activity | |
|---|---|---|---|---|
| WRAIR Sample # | Substitution | Dose (mg/kg) | Cures | Increase in survival (days) |
| Trypanocidal Activity of Compounds with Significant Activity | | | | |
| CLASS A. Substituents of the amido, carboxamidine, thiocarboxamide and amide oxime type | | | | |
| Subclass 1: Imidazo[1,2-a]pyridinium Salts | | | | |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|

Structure:

$$\text{pyridine ring fused imidazolium: positions } 5,6,7,8 \text{ on pyridine, N}^+ \text{ at position 1 with R}_1, \text{ N at position 4, C}_2 \text{ bonded to phenyl-X with Z}^-$$

| WRAIR Sample # | Substitution | Dose (mg/kg) | Cures | Increase in survival (days) |
|---|---|---|---|---|
| BJ36718 | $R_1 = CH_3$; $x = NHCOCH_3$; $Z = I^-$ | 212 | 3/5 | 6.5 |
| | | 106 | — | 4.4 |
| | | 53 | 4/5 | 8.0 |
| | | 424* | 8/10 | 11.0 |
| | | 212 | 4/5 | 1.1 |
| | | 106* | 7/10 | 7.0 |
| BJ58296 | $R_1 = CH_2CH=CH_2$; $x = NHCOCH_3$; $Z = Br^-$ | 26.5 | 7/10 | 5.0 |
| BJ83306 | $R_1 = CH_3$; $R_6 = I$; $x = NHCOCH_3$; $Z = TsO^-$ | 424 | 4/10 | 6.5 |
| | | 212 | 1/5 | 3.9 |
| | | 106 | 3/10 | 2.3 |
| BJ83315 | $R_1 = CH_3$; $x = NHCOCH_3$; $Z = TsO^-$ | 424 | 9/10 | 2.9 |
| | | 212 | 3/5 | 6.4 |
| | | 106 | — | 3.7 |
| BJ84974 | $R_1 = CH_3$; $x = C(=NOH)NH_2$; $Z = Cl^-$ | 212 | 5/5 | — |
| | | 106 | 9/10 | 9.9 |
| | | 53 | 5/5 | — |
| | | 26.5 | 2/10 | 1.6 |
| | | 13.3 | — | 3.1 |
| BJ84938 | $R_1 = CH_3$; $R_6 = CH_3$; $x = NHCOCH_3$; $Z = TsO^-$ | 424 | 7/10 | 8.5 |
| | | 212 | 1/5 | 5.9 |
| | | 106 | 1/10 | 1.3 |
| BJ90703 | $R_1 = CH_3$; $R_5 = CH_3$; $R_7 = CH_3$; $x = NHCOCH_3$; $Z = TsO^-$ | 424 | 3/5 | 9.4 |
| | | 106 | 4/5 | 2.9 |
| | | 26 | 1/5 | 8.9 |
| BJ90712 | $R_1 = CH_3$; $x = CH=NOH$; $Z = TsO^-$ | 424* | 1/5 | 3.4 |
| | | 106 | 2/5 | 4.2 |
| BJ90758 | $R_1 = CH_3$; $R_6 = CO_2CH_3$; $x = NHCOCH_3$; $Z = TsO^-$ | 424 | 2/10 | 4.2 |
| | | 106 | — | 4.2 |
| BK02566 | $R_1 = CH_2CH=CH_2$; $x = N(COCH_3)(CH_2CH_3)$; $Z = Br^-$ | 424* | 5/10 | 9.9 |
| | | 212* | 1/5 | 4.7 |
| | | 106* | 1/10 | 2.8 |
| BK02557 | $R_1 = CH_2CH=CH_2$; $R_6 = CH_3$; $x = NHCOCH_3$; $Z = Br^-$ | 424* | 2/10 | 3.8 |
| BK11743 | $R_1 = CH_3$; $x = C(=S)NH_2$; $Z = TsO^-$ | 212 | 4/5 | 17.0 |
| | | 106 | 5/10 | 3.2 |
| | | 53 | 5/5 | — |
| | | 26 | 3/15 | 4.0 |
| | | 13.3 | 1/10 | 3.3 |
| | | 6.65 | 2/10 | 2.7 |
| BK13087 | $R_1 = CH_3$; $R_6 = CH_3$; $x = C(=NOH)NH_2$; $Z = Cl^-$ | 53 | 2/5 | 2.3 |
| BK16471 | $R_1 = CH_3$; $x = C(=^+NH_2)NH_2$; $Z = 2Cl^-$ | 53 | 5/5 | — |
| | | 26.5 | 10/10 | — |
| | | 13.3 | 2/10 | 3.2 |
| BK23001 | $R_1 = CH_3$; $x = C(=^+NH_2)NHCH_2CH_2-^+N(C_2H_5)_2\cdot H$; $Z = 3Cl^-$ | 13.3 | — | 6.6 |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|
| BK42748 | $R_1 = CH_3$; $R_6 = C\begin{smallmatrix}+NH_2\\NH_2\end{smallmatrix}$ ; $x = C\begin{smallmatrix}+NH_2\\NH_2\end{smallmatrix}$  $Z = 2Cl^-$ | 53<br>26.5 | 2/5<br>2/5 | 3.0<br>2.3 |
| BK42757 | $R_1 = CH_3$; $R_3 = NO_2$; $x = C\begin{smallmatrix}+NH_2\\NH_2\end{smallmatrix}$ ; $Z = 2Cl^-$ | 106<br>53 | 1/5<br>1/5 | 3.0<br>2.5 |
| BK46166 | $R_1 = CH_3$; $R_6 = CH_3$; $x = C\begin{smallmatrix}+NH_2\\NH_2\end{smallmatrix}$ ; $Z = 2Cl^-$ | 106<br>53<br>26.5 | 2/5<br>2/5<br>2/5 | 5.2<br>1.6<br>4.5 |
| BK46193 | $R_1 = CH_3$; $R_6 = Cl$; $x = C\begin{smallmatrix}NOH\\NH_2\end{smallmatrix}$ ; $Z = Cl^-$ | 212<br>106 | 4/5<br>1/5 | 2.9<br>5.2 |

Subclass 2: Imidazo[2,1-b]thiazolium Salts

[Structure: imidazo[2,1-b]thiazolium with $R_1$ on N+, phenyl-X at position 2, $Z^-$ counterion; ring positions 5, 6 on thiazole side, 3, 4 on imidazole side]

| BK203010 | $R_1 = CH_3$; $x = C\begin{smallmatrix}//\\NHCH_2CH_2N(C_2H_5)_2\end{smallmatrix}$ ; $Z = Cl^-$ | 26.5 | 2/10 | 4.1 |
| BK16499 | $R_1 = CH_3$; $x = C\begin{smallmatrix}NOH\\NH_2\end{smallmatrix}$ ; $Z = Cl^-$ | 53<br>26 | 2/10<br>2/10 | 4.7<br>2.7 |
| BK21874 | $R_1 = CH_3$; $x = C\begin{smallmatrix}+NH_2\\NH_2\end{smallmatrix}$ ; $Z = 2Cl^-$ | 212<br>106<br>53<br>26.5 | 5/5<br>9/10<br>2/5<br>1/10 | —<br>12.9<br>2.5<br>3.6 |

Subclass 3: Other Heterocyclic Salts

[General structure: $^+R$—phenyl—X]

| BJ51911 | [5,6,7,8-tetrahydroimidazo[1,2-a]pyridinium with +N-CH_3]; $x = NHCOCH_3$; $Z = I^-$ | 106<br>53<br>26.5 | 3/10<br>—<br>1/10 | 7.4<br>6.4<br>1.2 |
| BJ83235 | [imidazo[2,1-a]isoquinolinium with +N-CH_3]; $x = NHCOCH_3$; $Z = I^-$ | 212<br>53 | 4/5<br>1/5 | 2.9<br>1.7 |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|
| BJ83244 | 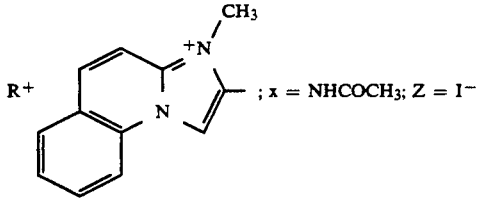 ; x = NHCOCH$_3$; Z = I$^-$ | 212 | 3/5 | 8.4 |
| BK22979 | 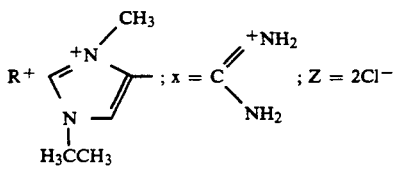 ; x = C(+NH$_2$)(NH$_2$) ; Z = 2Cl$^-$ | 212<br>106 | 1/5<br>1/10 | 2.5<br>4.5 |
| BK42739 | 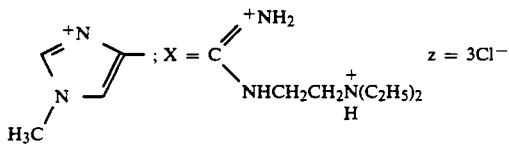 ; X = C(+NH$_2$)(NHCH$_2$N$^+$(C$_2$H$_5$)$_2$H) ; z = 3Cl$^-$ | 26 | 1/10 | 3.8 |

Subclass 4 of Class A Aryloxymethyl Heteroaromatic Rings $$^+R-CH_2O-\!\!\!\!\bigcirc\!\!\!\!-X\ Z^-$$

| BK65330 | 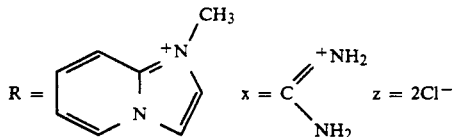 R = ; x = C(+NH$_2$)(NH$_2$) ; z = 2Cl$^-$ | 13.3<br>3.3<br>1.6 | 3/5<br>5/5<br>2/10 | 12<br>—<br>4.6 |

CLASS B. Substituents derived from the formyl group including semicarbazone, thiosemicarbazona, guanylhydrazone and substituted guanylhydrazone.

Subclass 1: imidazo[1,2-a]pyridinium salts

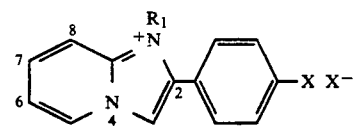

| BJ90721 | R$_1$ = CH$_3$; x = CH=NNHCSNH$_2$; Z = TsO$^-$ | 424<br>212<br>106<br>53<br>26<br>424* | 5/5<br>4/5<br>3/5<br>1/5<br>—<br>1/10 | <br>18.0<br>7.5<br>7.8<br>4.4<br>1.9 |
| BJ90730 | R$_1$ = CH$_3$; x = CH=NNHCONH$_2$; Z = TsO$^-$ | 106<br>26<br>424*<br>106* | 4/5<br>1/5<br>3/10<br>1/10 | 10.9<br>7.7<br>4.8<br>1.9 |
| BJ90749 | R$_1$ = CH$_3$; x = CH=NNHC(+NH$_2$)(NH$_2$) ; Z = 2TsO$^-$ | 13.3<br>6.6<br>3.3<br>1.60<br>0.83<br>0.42<br>0.21 | 10/10<br>5/5<br>5/5<br>10/10<br>8/10<br>2/10<br>1/5 | <br><br><br><br>6.2<br>5.4<br>2.5 |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|
| BK11770 | $R_1 = CH_2CH=CH_2; x = CH=NNHC\begin{matrix}^+NH_2\\ \\NH_2\end{matrix}$ ; $Z = 2Br^-$ | 13.3<br>1.66<br>0.83<br>0.42<br>0.21 | 5/5<br>3/5<br>5/5<br>4/5<br>3/5 | <br>5.5<br><br>17.0<br>7.5 |
| BK13069 | $R_1 = CH_3; R_6 = Cl; x = CH=NNHC\begin{matrix}^+NH_2\\ \\NH_2\end{matrix}$ ; $z = 2TsO^-$ | 6.65<br>3.33<br>1.66<br>0.83<br>0.42<br>0.21 | 5/5<br>5/5<br>10/10<br>10/10<br>2/5<br>2/5 | <br><br><br><br>7.7<br>7.0 |
| BK13078 | $R_1 = CH_3; R_6 = CH_3; x = CH=NHC\begin{matrix}^+NH_2\\ \\NH_2\end{matrix}$ ; $Z = 2TsO^-$ | 26.5<br>13.3<br>6.65<br>3.33<br>1.66<br>0.83<br>0.42<br>0.21<br>212*<br>106*<br>53*<br>26*<br>13*<br>6.6*<br>3.3 | 15/15<br>10/10<br>5/5<br>5/5<br>9/10<br>10/10<br>4/5<br>2/5<br>5/5<br>10/10<br>10/10<br>13/15<br>10/10<br>3/5<br> | <br><br><br><br>11.0<br><br>7.0<br>5.3<br><br><br><br><br><br>7.0<br>1.0 |
| BK46175 | $R_1 = CH_3; x = CH=NNHC\begin{matrix}^+NHCH_2CH_2NEt_2\\ \\NH_2\end{matrix}$ ; $Z = 2Br^-$ | 0.83<br>1.66 | M —<br>(F) 2/5 | 6.3<br>3.3 |
| BK46200 | $R_1 = CH_3; x = CH=NNHC\begin{matrix}^+NHCH_3\\ \\NH_2\end{matrix}$ ; $Z = 2Br^-$ | 3.33-6.65<br>0.85-1.66 | (F) 5/5<br>(M) 5/5 | |
| BK46219 | $R_1 = CH_3; R_7 = CH_3; x = CH=NNC\begin{matrix}^+NH_2\\ \\NH_2\end{matrix}$ ; $Z = 2TsO^-$ | 26.5<br>13.3<br>6.6<br>1.66<br>0.83 | 8/10<br>10/10<br>5/5<br>5/5<br>2/5 | 10.0<br><br><br>10.3<br> |
| BK47921 | $R_1 = CH_3; x = CH=NNHC\begin{matrix}^+NH_2\\ \\SCH_3\end{matrix}$ ; $Z = 2Br^-$ | 26.5 | 5/5 | |
| BK47958 | $R_1 = CH_3; R_3 = NO_2; x = CH=NNHC\begin{matrix}^+NHCH_3\\ \\NH_2\end{matrix}$ ; $Z = 2Br^-$ | 1.66<br>0.8<br>0.4 | 8/10<br>4/5<br>5/5 | 3.0<br>2.0<br> |
| BK47985 | $R_1 = CH_3; R_3 = NO_2; x = CH=NNC\begin{matrix}^+NH_2\\ \\NH_2\end{matrix}$ ; $Z = 2Br^-$ | 6.6<br>3.3<br>1.6 | 4/5<br>5/5<br>3/10 | 24.0<br><br>7.0 |
| BK47976 | $R_1 = CH_3; x = CH=NNHC\begin{matrix}^+NH_2\\ \\N(CH_3)_2\end{matrix}$ ; $Z = 2Br^-$ | 6.66<br>3.33<br>1.66<br>0.8<br>0.4<br>0.2 | 5/5<br>5/5<br>10/10<br>10/10<br>5/5<br>5/5 | |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|
| BK50277 | $R_1 = CH_3$; x = CH=NNHC(=+NH_2)(N-pyrrolidinyl); Z = 2Br− | 3.3<br>1.7<br>0.8<br>0.4<br>0.2<br>0.1<br>0.06 | 5/5<br>10/10<br>9/10<br>5/5<br>4/5<br>5/5<br>4/5 | <br><br>27.0<br><br><br>14.0<br> |
| BK51890 | $R_1 = CH_3$; x = CH=NNHC(=+NH_2)(N-morpholinyl); Z = 2Br− | 424*<br>106*<br>26*<br>13*<br>6.6*<br>3.3*<br>1.66* | 5/5<br>5/5<br>9/10<br>5/5<br>5/5<br>5/5<br>1/5 | <br><br><br><br><br><br>10.9 |

Subclass 2: Imidazo[2,1-b]thiazolium Salts

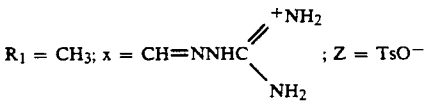

| BK21909 | $R_1 = CH_3$; x = CH=NNHC(=+NH_2)(NH_2); Z = TsO− | 13.3<br>6.65<br>3.33<br>1.66<br>0.83<br>0.42 | 5/5<br>10/10<br>10/10<br>4/5<br>4/5<br>4/5 | <br><br><br>5.0<br>5.0<br>2.0 |
| BK21918 | $R_1 = CH_3$; x = CH=NNHCONH_2; Z = TsO− | 26.5<br>53 | —<br>— | 4.8<br>4.5 |
| BK47967 | $R_1 = CH_3$; x = CH=NNHC(=+NHCH_3)(NH_2); Z = 2I− | 6.66<br>3.33<br>1.66<br>0.83<br>0.42 | 5/5<br>5/5<br>5/5<br>10/10<br>5/5 | |

Subclass 3: Other Heteroaromatic Rings

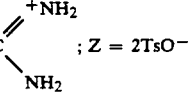

| BK16462 | $R^+$ = 1,4-dimethylpyrazinium; x = CH=NNHC(=+NH_2)(NH_2); Z = 2TsO− | 13.3<br>6.6<br>3.3<br>1.6<br>0.8<br>0.4<br>0.2 | 10/10<br>4/5<br>5/5<br>5/5<br>4/5<br>1/5<br>1/5 | <br>14.0<br><br><br>7.0<br>3.3<br>2.8 |
| BK23994 | $R^+$ = 1,4-dimethylpyrazinium; x = CH=NNHCONH_2; Z = TsO− | 424 | — | 5.8 |

Subclass 4 of Class B Aryloxymethyl Heteroaromatic Rings

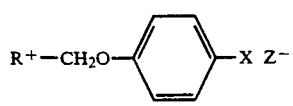

TABLE I-continued

Trypanocidal Activity of Compounds with Significant Activity

| WRAIR Sample # | Substitution | Dose (mg/kg) | Trypanocidal Activity | |
|---|---|---|---|---|
| | | | Cures | Increase in survival (days) |
| BK75087 | R = [imidazo[1,2-a]pyridinium-CH3], X = CH=NNHC(=+NH2)NHOH, z = 2Br⁻ | 6.6<br>0.8<br>0.4<br>0.2 | 5/5<br>10/10<br>3/5<br>2/5 | —<br>—<br>10<br>5.9 |
| BL03933 | R = [imidazo[1,2-a]pyridinium-CH3], X = CH=NNHC(=+NHC2H5)NHC2H5, z = 2Br⁻ | 6.6<br>3.3<br>1.6 | 5/5<br>5/5<br>7/10 | —<br>—<br>6.3 |
| BL28038 | R = [1,3-dimethylimidazolium], X = CH=NNHC(=NHC2H5)NHC2H5, z = 2Br⁻ | 13 | 3/5 | — |
| BL10018 | R = [1,3-dimethylbenzimidazolium], X = CH=NNH-(imidazolinium), z = 2Br⁻ | 6.6<br>1.6<br>0.4 | 5/5<br>10/10<br>3/5 | —<br>—<br>6.8 |
| BL07646 | R = [N-methylpyridinium], X = CH=NNH-(imidazolinium), z = 2Br⁻ | 13<br>6.6<br>1.6 | 9/10<br>3/5<br>1/10 | 4.0<br>9.9<br>3.9 |
| BL10027 | R = [N-methylpyridinium-3-yl], X = CH=NNHC(=+NH2)(pyrrolidinyl), z = 2Br⁻ | 13<br>3.3<br>0.8 | 5/5<br>5/5<br>7/10 | —<br>—<br>5.2 |
| BL12129 | R = [N-methylpyridinium-4-yl], X = CH=NNHC-(imidazolinium), z = 2Br⁻ | 13<br>3.3 | 8/10<br>1/5 | 5.0<br>6.8 |

Subclass 5 of class B. Arylethenyl Heteroaromatic Rings $$R^+CH-CH-\text{(C}_6\text{H}_4\text{)}-X\ Z^-$$

| BL09462 | R = [imidazo[1,2-a]pyridinium-CH3], x = CH=NNHC(=+NH2)NH2, Z = 2TsO⁻ | 0.8<br>0.2<br>0.1 | 10/10<br>5/5<br>6/10 | —<br>—<br>5.2 |

TABLE I-continued

Trypanocidal Activity of Compounds with Significant Activity

| WRAIR Sample # | Substitution | Dose (mg/kg) | Trypanocidal Activity Cures | Increase in survival (days) |
|---|---|---|---|---|
| BL12165 | 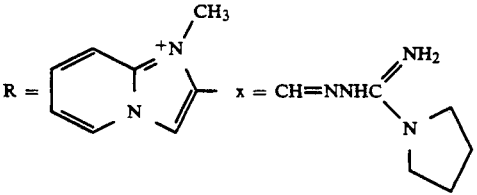 R = [imidazo[1,2-a]pyridine with N-CH₃]; x = CH=NNHC(NH₂)(N-pyrrolidinyl); Z = 2TsO⁻ | 26<br>13<br>3.3<br>1.6 | 15/15<br>10/10<br>2/5<br>6/10 | —<br>—<br>12.3<br>5.2 |
| BL11202 | 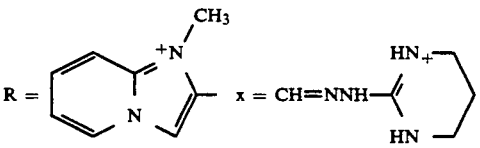 R = [imidazo[1,2-a]pyridine with N-CH₃]; x = CH=NNH—C(=NH⁺)(cyclic); Z = 2Br⁻ | 26<br>6.6<br>1.6<br>0.4 | 15/15<br>5/5<br>9/10<br>5/5 | —<br>—<br>6.8<br>— |
| BL21593 | 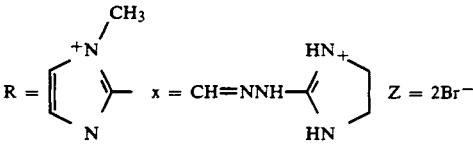 R = [N-CH₃ imidazolium]; x = CH=NNH—C(=NH⁺)(cyclic); Z = 2Br⁻ | 26<br>13<br>6.5 | 5/5<br>10/10<br>5/5 | —<br>—<br>— |
| BL21584 | 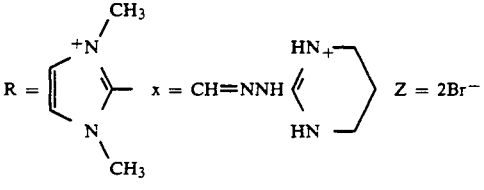 R = [N,N-diCH₃ imidazolium]; x = CH=NNH—C(=NH⁺)(cyclic); Z = 2Br⁻ | 13<br>6.6 | 10/10<br>5/5 | —<br>— |

CLASS C. substituents of the heterocyclic Type

Subclass 1: Imidazo[1,2-a]pyridines

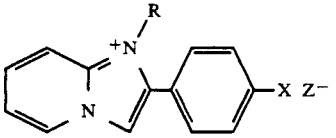

| BK24017 | R₁ = CH₂CH=CH₂; x = CH=NNH—[imidazoline]; Z = 2Br⁻ | 53<br>26 | —<br>4/10 | 4.6<br>2.3 |
| BK50302 | 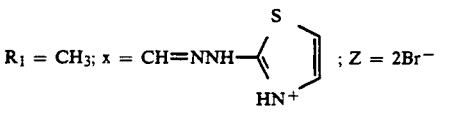 R₁ = CH₃; x = CH=NNH—[thiazoline HN⁺]; Z = 2Br⁻ | 0.8<br>0.4<br>0.2 | 4/5<br>5/5<br>3/5 | 15.0<br><br>2.0 |
| BK50311 | 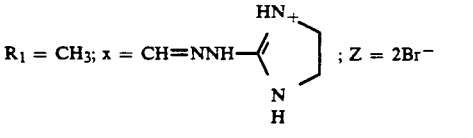 R₁ = CH₃; x = CH=NNH—[imidazoline HN⁺]; Z = 2Br⁻ | 13.3<br>6.6<br>3.3<br>1.66<br>0.83<br>0.42<br>424*<br>212*<br>106*<br>53*<br>26*<br>13.3* | 10/10<br>3/5<br>5/5<br>9/10<br>8/10<br>2/5<br>10/10<br>5/5<br>10/10<br>5/5<br>13/15<br>9/10 | <br>10.0<br><br>22.0<br>1.5<br>6.6<br><br><br><br><br>13.5<br>9.0 |

Subclass 2: Imidazo [2,1-B]thiazoles

TABLE I-continued
Trypanocidal Activity of Compounds with Significant Activity

| WRAIR Sample # | Substitution | Dose (mg/kg) | Cures | Increase in survival (days) |
|---|---|---|---|---|

Structure:
$$\text{bicyclic thiazole-imidazole with } R^+ \text{ on N, attached to phenyl-X } Z^-$$

| BK2403S | $R_1 = CH_3$; x = CH=NNH—[triazole-NH]; Z = 2Br$^-$ | 212 | 3/5 | 5.0 |
| | | 106 | 7/10 | 7.7 |
| | | 53 | 3/5 | 12.5 |
| | | 26.5 | 12/15 | 7.3 |
| | | 13.3 | 6/10 | 5.0 |
| | | 6.65 | 4/5 | 5.0 |
| | | 3.33 | 2/5 | 9.7 |
| BK42720 | $R_1 = CH_3$; x = [triazole-NH, $^+NH_3$]; Z = 3Cl$^-$ | 26.5 | 5/5 | |
| | | 13.3 | 10/10 | |
| | | 6.65 | 5/5 | |
| | | 3.33 | 5/5 | |
| BK62620 | $R_1 = CH_3$; x = CH=NNH—[cyclic amidine with HN$^+$, NH]; Z = 2Br$^-$ | 13.3 | 9/10 | 28.0 |
| | | 6.66 | 4/5 | 3.8 |
| | | 3.33 | 5/5 | |
| | | 1.66 | 9/10 | 9.0 |
| | | 0.83 | 8/10 | 8.9 |

Class D. Heteroaromatic Rings with Intervening Groups

Structure:
$$\text{pyridine-imidazo ring with } ^+N\text{-}CH_3, \text{ attached to phenyl-X-Y } Z^-$$

| BL07815 | X = CH=CH  Y = CH=NNHC(NH$_2$)=NH$_2$  Z = 2TsO$^-$ | 106 | 10/10 | — |
| | | 53 | 5/5 | — |
| | | 26 | 15/15 | — |
| | | 13 | 10/10 | — |
| | | 6.6 | 5/5 | — |
| | | 3.3 | 5/5 | — |
| | | 1.6 | 10/10 | — |
| | | 0.4 | 5/5 | — |
| BL07824 | X = CH=CH  Y = CH=NNH—[cyclic amidine with N$^+$H, NH]; Z = 2Br$^-$ | 13 | 5/5 | — |
| | | 6.6 | 5/5 | — |
| | | 3.3 | 5/5 | — |

TABLE 2

Peritonal Activity of Substituted Guanylhydrazones

[Structure: indolizine ring system with Polar group at para position of phenyl, and R-N+ substituent]

| Compound Number | Substituents Ring | Polar | Activity at Dosage (mg/kg) C = Cures | | | | | | | | |
|---|---|---|---|---|---|---|---|---|---|---|---|
| | | | 424 | 212 | 106 | 53 | 26 | 13 | 6.7 | 3.3 | 1.7 | 0.8 | 0.4 | 0.2 |
| BK90749 | H | CH=NNHC(=+NH₂)NH₂ | 10C/10 | 5C/5 | 5C/5 | 5C/5 | 10C/10 | 2C/5 (4.0) | — | — | — | — | — | — |
| BK13078 | 6-Me | CH=NNHC(=+NH₂)NH₂ | 8C/10 (12.5) | 5C/5 | 10C/10 | 5C/5 | 13C/15 (10.6) | 10C/10 | 3C/5 (7.0) | 3C/5 (1.0) | INAC | INAC | — | — |
| BK50268 | 3-NO₂ | CH=NNHC(=+NH₂)NH₂ | 4c/5 1TOX | 5c/5 | 8c/10 (12.5) | 4c/5 (9.9) | 7c/15 (5.0) | 1c/10 (4.5) | INAC | INAC | — | — | — | — |
| BK50302 | H | CH=NNH-(2-thiazolyl) | INAC | INAC | INAC | — | — | — | — | — | — | — | — | — |
| BK50311 | H | CH=NNH-(2-imidazolinyl) | 10C/10 | 5C/5 | 10C/10 | 5C/5 | 13C/15 (13.5) | 9C/10 (9.0) | 2C/5 (7.7) | 2C/5 (1.6) | (1.0) | — | — | — |
| BK51890 | H | CH=NNHC(=+NH₂)-morpholinyl | 5C/5 | — | 5C/5 | — | 9C/10 (5.9) | 5C/5 | 5C/5 | 5C/5 | 1C/5 (10.9) | INAC | — | — |

TABLE 2-continued
Peritonal Activity of Substituted Guanylhydrazones
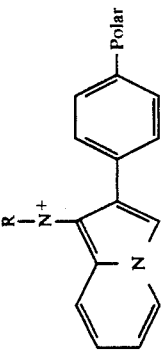
| Compound Number | Substituents Ring | Substituents Polar | Activity at Dosage (mg/kg) C = Cures | | | | | | | | |
|---|---|---|---|---|---|---|---|---|---|---|---|
| | | | 424 | 212 | 106 | 53 | 26 | 13 | 6.7 | 3.3 | 1.7 | 0.8 | 0.4 | 0.2 |
| BK51907 | 3-Br | CH=NNHC(=+NH₂)NH₂ | 9C/10 (2.0) | 5C/5 | 10C/10 | 5C/5 | 7C/10 (10.0) | 3C/10 (7.0) | (3.8) | (1.2) | INAC | INAC | — | — |
| BK51961 | 6-Me | CH=NNH-(pyrazole NH₂) | 5C/10 (6.0) | 1C/5 (6.3) | 1C/10 (5.5) | INAC | INAC | INAC | — | — | — | — | — | — |
| BK52002 | H | CH=NHN-(thiazole NH₂) | ACTY (5.9) | INAC (1.8) | INAC (1.2) | INAC (0.6) | INAC (0.2) | INAC | — | — | — | — | — | — |

What is claimed is:

1. A compound having the general formula:

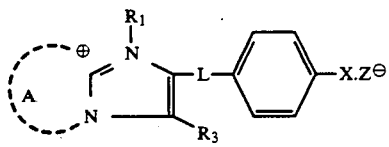

wherein A represents an optional heterocyclic ring fused to the imidazolium ring wherein the compounds are selected from the group consisting of

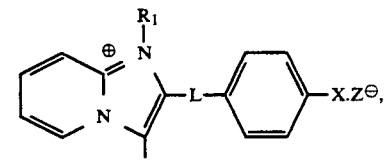

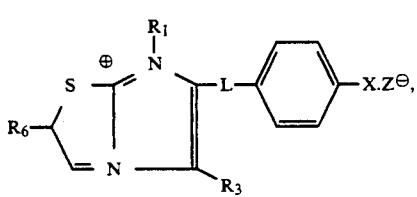

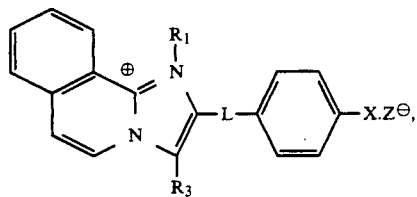

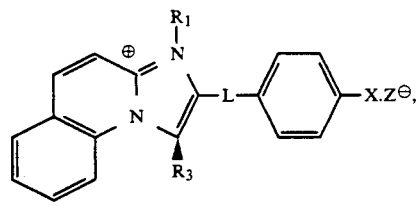

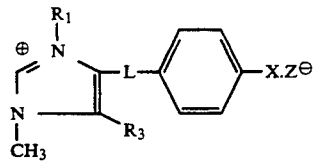

wherein $R_1$ is a straight or branched aliphatic group having from one to ten carbon atoms; $R_3$ represents $CH_3$, Br, hydrogen or $NO_2$;

Z represents I, Br, TsO or Cl;

L represents —$CH_2O$—, —CH=CH— or a single bond; and

X represents substituted guanylhydrazone or unsubstituted guanylhydrazone and $Z^\ominus$ represents an anion which forms a physiologically acceptable salt with the rest of the compound.

2. A compound according to claim 1 wherein A is a pyridine ring.

3. A compound according to claim 1 wherein A is a thiazole ring.

4. A compound according to claim 1 wherein A is a pyrimidine ring.

5. A compound according to claim 1 wherein $R_1$ is methyl.

6. A compound according to claim 1 wherein $R_1$ is propenyl.

7. A compound according to claim 1 wherein L is methyleneoxy.

8. A compound according to claim 1 wherein L is ethenyl.

9. A compound according to claim 1 wherein L comprises a single bond between the imidazolium ring and the phenyl group.

10. A compound according to claim 1 wherein X is a substituted or unsubstituted guanylhydrazone.

11. A compound according to claim 1 wherein X is a hydroxyguanylhydrazone.

12. The compound of claim 1 wherein $R_1$ and $R_3$ are methyl.

13. The compound of claim 1 wherein $R_1$ represents methyl, propenyl, ethyl or isopropyl.

14. The compound of claim 1 wherein X.Z represents
—CH=NNHC($NH_2$Br)$NH_2$,
—CH=NNHC(=$NH_2$TsO)$NH_2$,
—CH=NNHC(=$NHCH_2CH_2N(C_2H_5)_2$Br)$NH_2$,
—CH=NNHC(=$NHCH_3$Br)$NH_2$,
—CH=NNHC(=$NH_2$Br)N($CH_3$)$_2$,
—CH=NNHC(=$NHCH_3$I)$NH_2$,
—CH=NNHC(=$NH_2$Br)NHOH,
—CH—NNHC(=$NHC_2H_5$Br)NH$C_2H_5$ and —CH=CH—CH=NNHC(=$NH_2$TsO)$NH_2$.

15. The compound of claim 5 wherein the heteroaromatic ring moiety is

16. The quaternary heteroaromatic salt having the formula:

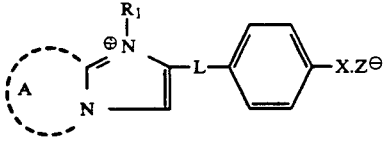

wherein A represents an optional heterocyclic ring fused to the imidazolium ring wherein

represents a group selected from a thiazole ring, a pyrimidine ring,

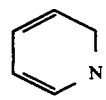

-continued

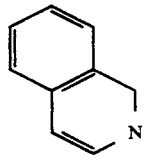

-continued

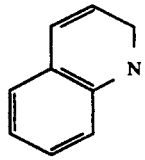

or ring A can be absent leaving the imidazolium ring to stand alone, wherein the heteroaromatic ring may be substituted at its various positions, wherein $R_1$ is a straight or branched aliphatic group having from one to ten carbon atoms; L represents —$CH_2O$—, —CH=CH— or a single bond; X represents substituted guanylhydrazone or unsubstituted guanylhydrazone; and Z represents an anion which forms a physiologically-acceptable salt with the rest of the compound.

17. A method of treating parasitic diseases in man and animals which comprises administering to infected humans or animals an effective amount of the compound of claim 1.

18. A method according to claim 17 wherein the compound is administered subcutaneously.

19. A method according to claim 17 wherein the compound is administered peritoneally.

20. A method according to claim 17 wherein the compound is administered at a dosage rate which comprises from about 0.2 to about 400 mg/kg.

* * * * *